United States Patent [19]

Byerley et al.

[11] Patent Number: 5,401,819
[45] Date of Patent: Mar. 28, 1995

[54] TRANS-BETA-ISOCYANATOACRYLATE ESTERS, THEIR PREPARATION, AND POLYMERS MADE THEREFROM

[75] Inventors: Thomas J. Byerley, Mission; Cecil C. Chappelow, Leawood; J. David Eick, Overland Park, all of Kans.

[73] Assignee: Curators of the University of Missouri, Columbia, Mo.

[21] Appl. No.: 289,064

[22] Filed: Aug. 11, 1994

Related U.S. Application Data

[62] Division of Ser. No. 864,236, Apr. 6, 1993, Pat. No. 5,347,044.

[51] Int. Cl.$^6$ .................. C08F 226/02; C08F 220/18; C07C 263/00
[52] U.S. Cl. ................... 526/301; 526/328.5; 560/343
[58] Field of Search ............... 526/301, 328.5; 560/343

[56] References Cited

U.S. PATENT DOCUMENTS 4,704,466  11/1987  Engel et al. ................. 558/411
4,876,323  10/1989  Engel et al. ................. 526/310

FOREIGN PATENT DOCUMENTS 0391556  10/1990  European Pat. Off.

OTHER PUBLICATIONS

Kircheldorf, "Angrew. Chem. Internat. Edit.", 1972, vol. 11, pp. 128–129.
Kircheldorf, "Makromonolokulare Chemic", 1973, vol. 173, pp. 13–41.
Washburne et al., Journal of Organic Chemistry, 1972, vol. 37, pp. 1738–1742.
"Organic Reaction", 1946, vol. 3, p. 342.
Byerley, et al., "Isocyanatoacrylates: A New Multifunctional Adhesive: Monomer Synthesis and Polymerization", Mar. 8, 1990, p. 3.
Byerley, et al., Journal of Dental Research Abstracts, "Isocyanato acrylates; A New Multifunctional Adhesive: Monomer Synthesis and Polymerization", 1990, p. 116, Abstract No. 59.
Rolf H. Prager and Stephen T. Were Aust. J. Chem., 1991 44, 1635–1641.

*Primary Examiner*—Joseph L. Schofer
*Assistant Examiner*—Wu C. Cheng
*Attorney, Agent, or Firm*—Shook, Hardy & Bacon

[57] ABSTRACT

Novel trans-beta-isocyanatoacrylate esters, their preparation and use in forming novel polymeric compositions, including polymers useful as adhesives, are disclosed. The trans-beta-isocyanatoacrylate esters have the formula:

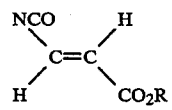

wherein R is $C_1$–$C_{18}$ linear or branched alkyls; $C_5$–$C_6$ cycloalkyl; aryl; alkaryl; aralkyl; $C_1$–$C_{18}$ halogenated alkyl; halogenated aryl; $C_1$–$C_8$ alkoxyalkyl; or alkoxyaryl.

9 Claims, 1 Drawing Sheet

TRANS-BETA-ISOCYANATOACRYLATE ESTERS, THEIR PREPARATION, AND POLYMERS MADE THEREFROM

This is a divisional of application Ser. No. 07/864,236, filed on April 6, 1993, now U.S. Pat. No. 5,347,044.

BACKGROUND OF THE INVENTION

The government has certain rights in this invention pursuant to research grant number NIDR RO1 DEO8223.

This invention relates generally to compositions of matter and, more particularly, to trans-beta-isocyanatoacrylate esters, their preparation, and polymers made from such esters. The polymers have utility, including as adhesives for living tissue and inanimate objects.

Certain α-substituted isocyanato esters and intermediates have previously been disclosed in U.S. Pat. Nos. 4,704,466 and 4,876,323. The esters disclosed in those patents were of the structure:

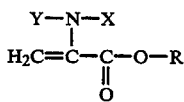

where X and Y were selected from one of the following pairs:

$X = CO_2C_2H_5$ and $Y = Si(CH_3)_3$;
and
$X = CO$ and $Y = $ none and R was selected from $C_{20}$ or lower, linear or branched alkyls; aryl; alkaryl; aralkyl; halogenated alkyl ($C_{20}$ or lower): halogenated aryl; alkoxyalkyl; and alkoxyaryl. The α-substituted isocyanato esters were disclosed to have utility in the preparation of adhesive compositions, such as for use in the joining of living tissue.

The present inventors have previously reported a process in which trans-beta-isocyanatoacrylate esters in solution were believed to have been prepared. Attempts to isolate and positively identify these esters were unsuccessful because they were unstable in the trans- configuration and readily isomerized to the cis-configuration. The cis- esters then readily cyclized to form N-carboxy-anhydride 1,3-oxazine-2,4(6H)-dione with loss of the isocyanate functionality. Although it was reported that the presence of an acid chloride impurity in the solution caused the trans- esters to be stabilized at room temperature, it was not felt that the esters would remain stable with the addition of heat for distillation purposes, particularly since it was well known that acids which are capable of forming anhydrides readily cyclize upon heating.

There have also been other reports of methods in which various beta-isocyanate-type compounds in solution were believed to have been produced. In each of these methods, however, the isocyanatoacrylate esters were not isolated from the solution. For example, Kircheldorf in *Angrew, Chem. Internat. Edit* Vol. 11, pages 128–129 (1972) prepared a beta-isocyanatocrotonic ester and showed that the isocyanate was present in the liquid phase. The isocyanate, however, was unstable and readily cyclized to 2-ethyl-1,3-oxazine-6-one.

Kircheldorf in *Makromolekulare Chemie* Vol. 173, pages 13–41 (1973) and Washburne et al. in *J. Org. Chem.* Vol. 37, pages 1938–42 (1972) have disclosed the preparation of beta-isocyanatoacrylic acids from maleic anhydride. The isocyanate intermediary was shown to be present but was destroyed during ring closing and was not isolated.

In *Organic Reaction* Vol. 3, page 342 (1946) the work of Curtius and Rodenhausen as originally reported in *J. Prakt. Chem.* Vol. 52, page 433 (1895) showed that isocyanates were prepared from fumaric acid but the free isocyanate was not isolated.

SUMMARY OF THE INVENTION

It is an object of this invention to isolate and positively identify a class of compounds characterized by an isocyanate substitution at a beta- position on certain acrylate esters.

It is also an object of this invention to provide a method for the synthesis and purification of trans-beta-isocyanatoacrylate esters useful in the preparation of polymeric compounds having utility as adhesives, including as dental adhesives and tissue adhesives.

It is a further object of this invention to provide an effective, non-toxic adhesive for tissue and inanimate objects, which adhesive is the polymeric product of the novel trans-beta-isocyanatoacrylate esters.

To accomplish these and other related objects, the invention in one aspect is directed to substantially pure trans-beta-isocyanatoacrylate esters, notably those having a purity of greater than 90% and being substantially free of liquid diluents.

In another aspect, the invention is directed to a method of isolating and purifying the trans-beta-isocyanatoacrylate esters, which method includes the steps of contacting a solution containing a mono-trans-azidofumarate with an excess of an isomerization catalyst under conditions sufficient to prevent isomerization of the mono-trans-azidofumarate to the cis-configuration and then subsequently processing the solution under conditions sufficient to prepare and isolate the trans-beta-isocyanatoacrylate ester compound. Notably a substantially pure, i.e. having a purity of 90% or greater, including as high was 95% purity, trans-beta-isocyanatoacrylate ester can be prepared by this method.

In a still further aspect, the invention is directed to the use of the trans-beta-isocyanatoacrylate esters in the preparation of novel polymers, including those having utility as adhesives.

BRIEF DESCRIPTION OF THE FIGURES

In the accompanying figures which form a part of the specification.

DETAILED DESCRIPTION OF THE INVENTION

Figure 1:
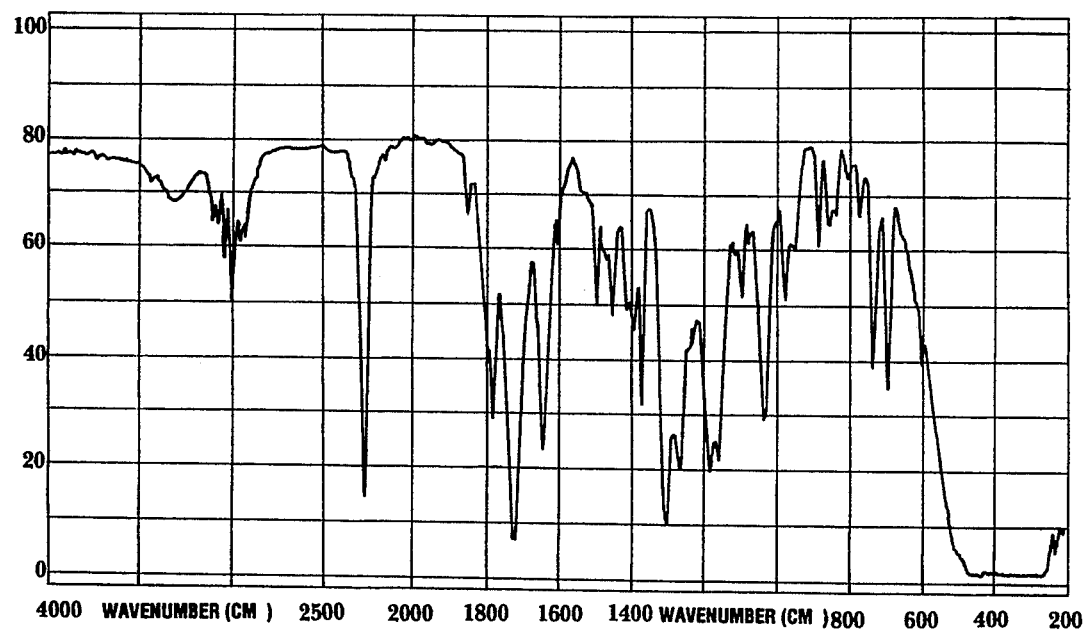
FIG. 1 is an infrared spectrum of purified ethyl trans-beta-isocyanatoacrylate in accordance with the present invention.
Figure 2:
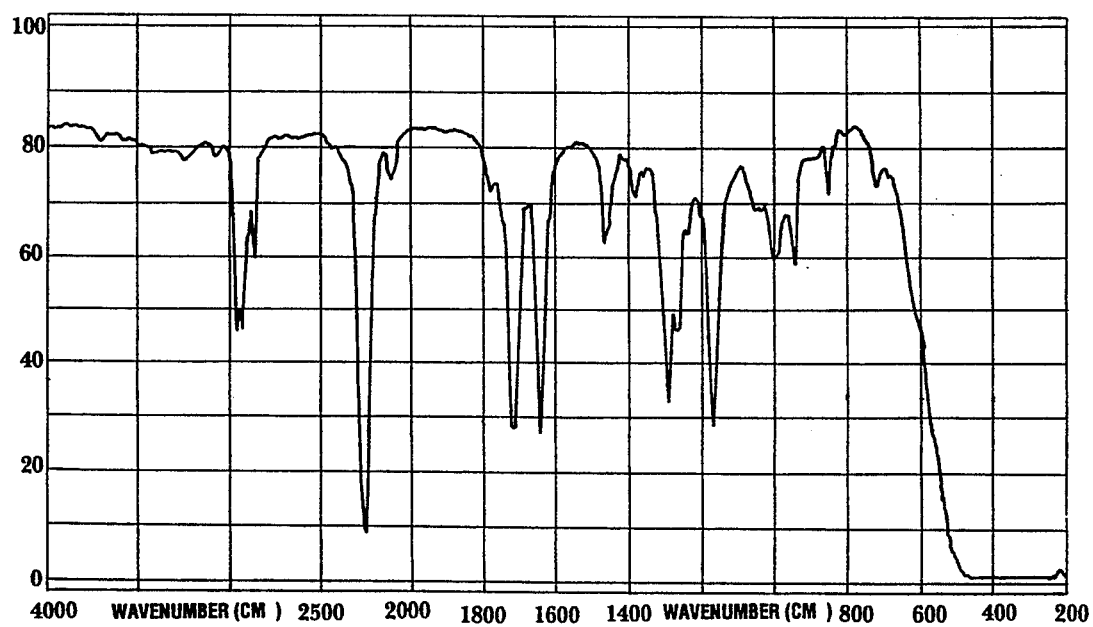
FIG. 2 is an infrared spectrum of purified n-hexyl trans-beta-isocyanatoacrylate in accordance with the present invention.

The trans-beta-isocyanatoacrylate esters of the present invention are monomers represented by the following general formula:

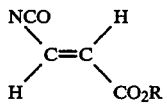

wherein R is $C_1$–$C_{18}$ linear or branched alkyl; $C_5$–$C_6$ cycloalkyl; aryl; alkaryl; aralkyl; $C_1$–$C_{18}$ halogenated alkyl; halogenated aryl; $C_2$–$C_8$ alkoxyalkyl; or alkoxyaryl. Especially preferred are compounds wherein R is $C_1$–$C_8$ linear or branched alkyl; $C_6$ cycloalkyl; or $C_3$–$C_6$ alkoxyalkyl. In accordance with the present invention, the novel trans-beta-isocyanatoacrylate esters are compounds which are substantially free of liquid diluents and can have a purity greater than 80%. Desirably, the trans-beta-isocyanatoacrylate esters are substantially pure. The term "substantially pure" as used herein means having a purity greater than approximately 90%, including as high as 95% or greater.

The trans-beta-isocyanatoacrylate esters can be prepared in accordance with the following reaction scheme:

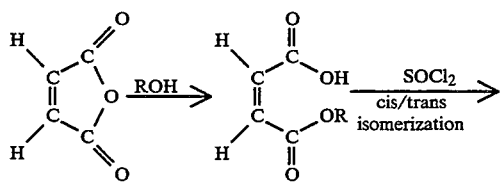

wherein R is as previously defined.

The method of preparing the trans-beta-isocyanatoacrylate esters includes the steps of contacting maleic anhydride with a suitable alcohol to open the ring and form the cis-monomaleate half esters. Equal molar quantities of the maleic anhydride and the alcohol are generally preferred. The ester is then contacted with thionyl chloride to form a trans-monofumarate or beta-substituted acrylic acid ester in yields as high as 75 to 90%. The process to this point has previously been exemplified by Dymicky in *Organic Preparations and Procedures Int.* Vol. 17, pages 121–131 (1985), which is incorporated herein by reference.

The monofumarates are converted to acid azides, notably trans-beta-azidofumarates, by contacting a water immiscible organic solution of the monofumarates with a suitable phase change catalyst such as tricaprylyl methyl ammonium chloride (available under the trademark Aliquat 336 from Aldrich Chemical Co.) and an aqueous solution of $NaN_3$. Suitable solvents for the monofumarates include aromatic and halogenated organic solvents such as toluene and methylene chloride. Examples of other suitable phase change catalysts include tetrabutyl ammonium bromide. Reaction conditions generally include room temperature and ambient pressure.

Following conversion of the monofumarates to the acid azides by exchange of the azido moiety for the chloro moiety, the water phase of the reaction mixture is separated and the organic phase is washed with water to remove any residual inorganic salts. The organic layer is then dried over anhydrous sodium sulfate ($Na_2SO_4$) and filtered. It is important that the azides are not separated at this point because they can decompose violently.

While the process of forming isocyanates by the thermal decomposition of acyl azides is well known as the Curtius Reaction, previous attempts to form stable trans-beta-isocyanatoacrylate esters from the acid azides have met with failure because the trans-beta-isocyanatoacrylate esters which are believed formed using this process are unstable and isomerize to the cis-configuration which readily cyclizes with destruction of the isocyanate functionality. It was previously reported by the present inventors that the acid chloride when present as an impurity in the product solution

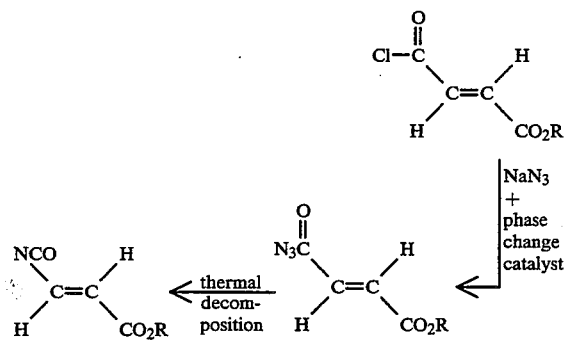

appeared to stabilize the trans-beta-isocyanatoacrylate esters in solution but it was not known that the esters could remain stabilized while attempting distillation separation. In fact, it was expected that the esters could not be separated in this fashion because it was well known that acids that are capable of forming anhydrides readily cyclize upon heating. In addition, improvements in the method of obtaining the azides by utilizing a phase change catalyst in an aqueous organic medium in place of a process in which an anhydrous medium has been used, resulted in significantly greater yields of the azide. However, when the azide was thermally decomposed to the isocyanate, the product cyclized and could not be maintained even at room temperature. Although it is now believed that the product could not be stabilized because the process improvements had eliminated the acid chloride impurity, the cause of the product instability was previously believed to be due to other factors.

Despite the prior belief that the trans-beta-isocyanatoacrylate esters would not remain stable upon heating even in the presence of the acid chloride impurity, it has been unexpectedly discovered that an amount of an isomerization catalyst such as the acid chloride or other acid halide, will sufficiently stabilize the esters to permit isolation of the esters by distillation separation. Surprisingly, the purity obtainable for the isolated esters can be greater than 90% including as high as 95% or higher. The amount of acid halide required to stabilize the esters during distillation heating can be as little as approximately one percent, or less, by weight based on the weight of the esters. Larger amounts of the acid halide can be used if desired.

The acid halides can be added to the product solution prior to distillation or can be formed in situ during the earlier process steps. Suitable acid halides can include acid chlorides such as fumaryl chloride and acid bromides such as fumaryl bromide. When formed in situ, thionyl chloride is the preferred reagent but other suitable reagents such as the phosphorous chlorides can also be used.

An excess of an acid halide should also be present during the thermal decomposition of the azide to the desired trans-beta-isocyanatoacrylate ester to prevent the isomerization of the ester to the unstable cis-configuration which readily cyclizes to form 1,3-oxazine-6-one. The acid chloride stabilizes the trans-beta-isocyanatoacrylate ester to such an extent that it can be stored at room temperature for an extended period of time, including up to or longer than a period of six years, without cyclization.

The beta-isocyanatoacrylate esters of the present invention have utility, including to produce new polymers, copolymers, adhesive compositions, cross-linking agents, and dye acceptor additives to vinylic polymers. The adhesive compositions are believed to have particular utility in the joining of live tissue, both plant and animal. The adhesives can be used in conjunction with the closing of surgical incisions, repairing broken bones, skin grafting (including synthetic skin) and implacement of prosthesis devices. The isocyanato group covalently bonds to tissue to form adhesive bonds which are metabolized slowly by living substances.

The trans-beta-isocyanatoacrylate esters can be homopolymerized such by contact with a suitable initiator, including free radical catalysts such as hydrogen peroxide, benzoyl peroxide or alpha,alpha'-azobisisobutyronitrile. The novel homopolymeric compositions formed from such reaction are believed to have particular utility as adhesives and matrix materials.

The trans-beta-isocyanatoacrylate esters can be copolymerized such by contact with other vinyl monomers such as alkyl acrylates, alkyl methacrylates and nitrogen containing monomers in the presence of a free radical initiator such as hydrogen peroxide, benzoyl peroxide or alpha,alpha'-azobisisobutyronitrile. The novel copolymeric compositions formed from such reactions are believed to have particular utility as adhesives.

It will be appreciated that R can be varied in the beta-isocyanatoacrylate esters to produce polymerization products which have characteristics desired for particular applications. For example, when the polymer is intended for usage as a structural adhesive, it is desirable to formulate the polymer so that it has good spreadability and wetting of the bonding surfaces. These properties can be achieved when R is generally within the range of $C_5$ to $C_8$. In other applications, such as for use as matrix resins for composite compositions, the desired properties can be obtained when R is $C_1$ to $C_4$.

The following examples are illustrative of the invention and are not intended to limit the scope thereof.

EXAMPLES

Example 1

Methyl trans-beta-isocyanatoacrylate

Equal molar quantities of methanol and maleic anhydride were reacted together. The half ester product was determined to be in the cis- configuration and was isomerized to the trans-configuration using $SOCl_2$. The trans- mono ester was converted to the acid chloride using $SOCl_2$. The acid chloride was purified by vacuum distillation. The azide was then prepared according to the following procedure. The stoichiometric equivalent of sodium azide plus 0.10 percent excess was dissolved in a minimum amount of water. This aqueous solution was added to 10× volume of toluene containing 1 volume percent phase change catalyst (Aliquat 336). The toluene/water mixture was stirred and cooled to 0°–5° C. in an ice bath. A solution of approximately 50 volume percent of this acid chloride in the same organic liquid was added slowly while keeping the temperature below 10° C. After addition, the mixture was stirred slowly and allowed to come to room temperature (25°–28° C). The water phase was separated and the organic layer was washed twice with water. After washing, the organic phase was dried over anhydrous sodium sulfate, preferably overnight. The dried solution was filtered and the filter residue was washed with toluene. To the filtrate was added fumaroyl chloride and the resulting solution was heated to achieve decomposition of the azide and rearrangement to the resultant isocyanate. The reaction mixture was heated until nitrogen evolution ceased. The solvent was removed under vacuum and the isocyanate product was isolated as a clear mobile fluid by fractional distillation. The yield of isocyanate product based on the nitrogen liberated ranged from 75 to 95% of theory. During the isomerization and distillation, it was necessary to maintain a level of about 1 weight percent acid chloride (based on the weight of the isocyanate) present in the isocyanate to prevent isomerization to the cis- isocyanate acrylate and intramolecular cyclization.

Example 2

Ethyl trans-beta-isocyanatoacrylate

The procedure of Example 1 was followed with the substitution of ethanol for methanol in order to form ethyl trans-beta-isocyanatoacrylate.

Example 3 n-Hexyl trans-beta-isocyanatoacrylate

The procedure of Example 1 was followed with the substitution of n-hexanol for methanol in order to form n-hexyl trans-beta-isocyanatoacrylate.

Example 4

Cyclohexyl trans-beta-isocyanatoacrylate

The procedure of Example 1 was followed with the substitution of cyclohexanol for methanol in order to form cyclohexyl trans-beta-isocyanatoacrylate.

Example 5

Benzyl trans-beta-isocyanatoacrylate

The procedure of Example 1 was followed with the substitution of benzyl alcohol for methanol in order to form benzyl trans-beta-isocyanatoacrylate.

Example 6

2-Methoxyethyl trans-beta-isocyanatoacrylate

The procedure of Example 1 was followed with the substitution of 2-methoxyethyl alcohol for methanol in order to form 2-methoxyethyl trans-beta-isocyanatoacrylate.

Example 7

2-Ethoxyethyl trans-beta-isocyanatoacrylate

The procedure of Example 1 was followed with the substitution of 2-ethoxyethyl alcohol for methanol in order to form 2-ethoxyethyl trans-beta-isocyanatoacrylate.

Example 8

2-Butoxyethyl trans-beta-isocyanatoacrylate

The procedure of Example 1 was followed with the substitution of 2-butoxyethyl alcohol for methanol in order to form 2-butoxyethyl trans-beta-isocyanatoacrylate.

Example 9

Poly(methyl beta-isocyanatoacrylate)

The title compound from example 1 is homopolymerized by adding 4 weight percent azobisisobutyronitrile and heating the resultant argon-purged reaction mixture for 24 hours at 80° C. The solid reaction mass is titrated with dry acetone, filtered, washed with hexane and dried in vacuo at 60° C. to obtain the homopolymer poly(methyl beta-isocyanatoacrylate).

Example 10

Ethyl beta-isocyanatoacrylate/Styrene Copolymer

The title compound from example 2 is bulk copolymerized by dissolving 0.1 parts of azobisisobutyronitrile in an argon-purged mixture of 1.4 parts of ethyl beta-isocyanatoacrylate and 1.0 parts of styrene, all parts being by weight. The resultant reaction mixture is held at 80° C. for 24 hours. The semi-solid reaction mass is titrated with 20 parts of dry acetone, filtered, washed with 100 parts of hexane and dried in vacuo at 60° C. to obtain the ethyl beta-isocyanatoacrylate/styrene copolymer.

Having thus described the invention, what is claimed is:

1. A method of preparing and purifying a trans-beta-isocyanato-acrylate ester comprising the steps of:
   thermally decomposing a trans-beta-azidofumarate ester in the presence of an isomerization catalyst under conditions sufficient to prepare said trans-beta-isocyanatoacrylate ester in solution; and
   processing said solution in the presence of said isomerization catalyst to remove said trans-beta-isocyanatoacrylate ester from said solution to obtain said purified trans-beta-isocyanatoacrylate ester.

2. The method of claim 1, wherein said step of thermally decomposing a trans-beta-azidofumarate ester in the presence of an isomerization catalyst comprises the step of providing an excess of an acid chloride as said isomerization catalyst.

3. The method of claim 1, wherein said step of thermally decomposing a trans-beta-azidofumarate ester in the presence of an isomerization catalyst comprises the step of providing an excess of fumaryl chloride or fumaryl bromide.

4. The method of claim 3, wherein said step of providing an excess of fumaryl chloride or fumaryl bromide comprises the step of adding an amount of said fumaryl chloride or fumaryl bromide to a solvent containing said trans-beta-azidofumarate ester.

5. A copolymer comprising the reaction product of a trans-beta-isocyanatoacrylate ester and styrene.

6. The copolymer of claim 5, wherein said trans-beta-isocyanatoacrylate ester is a substantially pure trans-beta-isocyanatoacrylate ester.

7. The copolymer of claim 6, wherein said trans-beta-isocyanatoacrylate ester comprises ethyl trans-beta-isocyanatoacrylate.

8. A homopolymer containing a trans-beta-isocyanatoacrylate ester repeating unit.

9. The homopolymer of claim 8, wherein said repeating unit comprises methyl trans-beta-isocyanatoacrylate.

* * * * *